Q2

US007498128B2

(12) United States Patent
Watkins

(10) Patent No.: US 7,498,128 B2
(45) Date of Patent: Mar. 3, 2009

(54) METHODS OF DETERMINING CONTRIBUTIONS TO METABOLIC PATHWAYS

(75) Inventor: Steven M. Watkins, Sacramento, CA (US)

(73) Assignee: Lipomics Technologies, Inc., West Sacramento, CA (US)

(*) Notice: Subject to any disclaimer, the term of this patent is extended or adjusted under 35 U.S.C. 154(b) by 0 days.

(21) Appl. No.: 11/296,829

(22) Filed: Dec. 6, 2005

(65) Prior Publication Data

US 2006/0084129 A1 Apr. 20, 2006

Related U.S. Application Data

(63) Continuation of application No. 10/615,966, filed on Jul. 9, 2003, now abandoned, which is a continuation of application No. 10/383,671, filed on Mar. 7, 2003, now abandoned.

(60) Provisional application No. 60/436,192, filed on Dec. 24, 2002, provisional application No. 60/424,949, filed on Nov. 8, 2002, provisional application No. 60/401,684, filed on Aug. 6, 2002, provisional application No. 60/373,912, filed on Apr. 19, 2002, provisional application No. 60/363,587, filed on Mar. 11, 2002.

(51) Int. Cl.
 *C12Q 1/00* (2006.01)
(52) U.S. Cl. .................................. 435/4; 435/15; 435/18
(58) Field of Classification Search ...................... 435/4, 435/15, 18; 436/71; 564/293
See application file for complete search history.

(56) References Cited

U.S. PATENT DOCUMENTS

| 5,709,888 | A | 1/1998 | Gil et al. |
| 5,869,304 | A | 2/1999 | Dickson et al. |
| 6,248,553 | B1 | 6/2001 | Small et al. |
| 2002/0009740 | A1 | 1/2002 | Kaddurah-Daouk et al. |
| 2002/0119462 | A1 | 8/2002 | Mendrick et al. |
| 2003/0175923 | A1 | 9/2003 | Tang et al. |
| 2003/0190671 | A1 | 10/2003 | Leyland-Jones |
| 2004/0024065 | A1 | 2/2004 | Watkins et al. |
| 2004/0143461 | A1 | 7/2004 | Watkins |
| 2005/0009005 | A1 | 1/2005 | Watkins |
| 2006/0088860 | A1 | 4/2006 | Watkins et al. |
| 2006/0141550 | A1 | 6/2006 | Watkins et al. |
| 2007/0026109 | A1 | 2/2007 | Foulger |

FOREIGN PATENT DOCUMENTS

| WO | WO-03/005628 A2 | 1/2003 |
| WO | WO-03/005628 A3 | 1/2003 |
| WO | WO-03/078574 A2 | 9/2003 |
| WO | WO-03/078574 A3 | 9/2003 |

OTHER PUBLICATIONS

Reo N. et al. Kinetic Analyses of Liver Phosphatidylcholine and Phosphatidylethanolamine Biosynthesis Using 13 C NMR, Spectroscopy. Biochimica et Biophysica Acta 1580(2-3)171-188, 2002.*
DeLong C. et al. Molecular Distinction of Phosphatidylcholine Synthesis Between the CDP Choline Pathway and Phosphatidylethanolamine Methylation Pathway. J of Biological Chemistry 274(42)29683-88, Oct. 15, 1999.*
Watkins S. et al. Unique Phospholipid Metabolism in Mouse Heart in Response to Dietary Docosahexaenoic or Alpha Linolenic Acids. Lipids 36(3)247-254, Mar. 2001.*
Henneberry A. et al. The Major Sites of Cellular Phospholipid Synthesis . . . Molecular Biology of the Cell vol. 13 3148-61, Sep. 2002.*
Agellon, L.B. et al. (Sep. 1999). "The Unique Acyl Chain Specificity of Bilary Phosphaatidylcholines in Mice is Independent of Their Biosynthetic Origin in the Liver," *Hepatology* 30(3):725-729.
Audubert, F. et al. (1984). "Fatty Acids Inhibit *N*-Methylation of Phosphatidylethanolamine in Rat Hepatocytes and Liver Microsomes," *Biochemica et Biophysica Acta* 792:348-357.
Berneis, K.K. et al. (Sep. 2002). "Metabolic Origins and Clinical Significance of LDL Heterogeneity," *J. Lipid Res.* 43:1363-1379.
Conner, A. (1981). "A Simple Method for the Preparation of Phosphatidylcholine Labeled at 2-Acyl Position," *Preparative Biochemistry* 11(1):91-97.
DeLong, C.J. et al. (Oct. 15, 1999). "Molecular Distinction of Phosphatidylcholine Synthesis Between the CDP-Choline Pathway and Phosphatidylethanolamine Methylation Pathway," *J. Biol. Chem.* 274(42):29683-29688.
Demacker, P.N.M. et al. (1997). "Precipitation Methods for High-Density Lipoprotein Cholesterol Measurement Compared, and Final Evaluation Under Routine Operating Conditions of a Method with a Low Sample-To-Reagent Ratio," *Clin. Chem.* 43(4):663-668.
Folch, J. et al. (1957). "A Simple Method for the Isolation and Purification of Total Lipides from Animal Tissues," *J. Biol. Chem.* 226:497-509.
Gibson, J.C. et al. (1984). "Precipitation of Apo E-Containing Lipoproteins by Precipitation Reagents for Apolipoprotein B," *Clin. Chem.* 30(11):1784-1788.
Holub, B.J. et al. (1987). "Nutritional Regulation of Cellular Phosphatidylinositol," in *Methods in Enzymology*, Conn, P.M. et al. eds., Academic Press, Inc.: Orlando, FL, 141:234-243.
International Search Report mailed Jul. 16, 2003 for PCT Application No. PCT/US03/07150 filed Mar. 7, 2003, five pages.
Kent, C. (1990). "Regulation of Phosphatidylcholine Biosynthesis," *Prog. Lipid Res.* 29(2):87-105.
Kent, C. (1995). "Eukaryotic Phospholipid Biosynthesis," *Annu. Rev. Biochem.* 64:315-343.
Konrad, S. (1998). "Use of Deuterium Oxide to Measure De Novo Fatty Acid Synthesis in Normal Subjects Consuming Different Dietary Fatty Acid Composition," *Biochem. Biophys. Acta* 1393(1):143-152.
Lieber, C.S. (2000). "Hepatic, Metabolic, and Nutritional Disorders of Alcoholism: From Pathogenesis to Therapy," *Crit. Rev. Clin. Lab. Sci.* 37(6):551-584.

(Continued)

*Primary Examiner*—Ralph Gitomer
(74) *Attorney, Agent, or Firm*—Morrison & Foerster LLP

(57) ABSTRACT

The present invention provides methods for assessing contribution of one or more pathways to the biosynthesis of a metabolite, e.g., a lipid using the levels of the product made and the metabolite precursors for each pathway.

19 Claims, No Drawings

OTHER PUBLICATIONS

Lieber, C.S. (Nov. 2001). "Alcoholic Liver Injury: Pathogenesis and Therapy in 2001," *Pathol. Biol.* (Paris) 49(9):738-752.

Lieber, C.S. et al. (May/Jun. 1994). "Hepatic Phosphatidylethanolamine Methyltransferase Activity is Decreased by Ethanol and Increased by Phosphatidylcholine," *Alcohol Clin. Exp. Res.* 18(3):592-595.

Miller, E. et al. (May 28, 1981). "Elevated Maternal Hemoglobin $A_{1c}$ in Early Pregnancy and Major Congenital Anomalies in Infants of Diabetic Mothers," *N. Engl. J. Med.* 304(22):1331-1334.

Moley, K.H. et al. (Dec. 1998). "Hyperglycemia Induces Apoptosis in Pre-implatation Embryos Through Cell Death Effector Pathways," *Nature* 4(12):1421-1424.

Nishimaki-Mogami, T. et al. (2002). "Inhibition of Phosphatidylcholine Synthesis via the Phosphatidylethanolamine Methylation Pathway Impairs Incorporation of Bulk Lipids into VLDL in Cultured Rat Hepatocytes," *J. Lipid Res.* 43:1035-1045.

Noga, A.A. et al. (Nov. 1, 2002). "An Unexpected Requirement for Phosphatidylethanolamine *N*-Methyltransferase in the Secretion of Very Low Density Lipoproteins," *J. Biol. Chem.* 277(44):42358-42365.

Okada, M. et al. (2001). "Direct Measurement of HDL Cholesterol: Method Eliminating Apolipoprotein E-Rich Particles," *J. Clin. Lab. Anal.* 15:223-229.

Pagano, R. et al. (1985). "Defining Lipid Transport Pathways in Animal Cells," *Science* 229(4718):1051-1057.

Pelech, S.L. et al. (Jun. 1984). "Regulation of Phosphatidylcholine Biosynthesis," *Biochim. Biophys. Acta* 779:217-251.

Reo, N.V. et al. (2002). "Kinetic Analyses of Liver Phosphatidylcholine and Phosphatidylethanolamine Biosynthesis Using $^{13}$C NMR Spectroscopy," *Biochim. Biophys. Acta* 1580(2-3):171-188.

Ruiz, J.I. et al. (1997). "Quantification in the Subnanomolar Range of Phospholipids and Neutral Lipids by Monodimensional Thin-layer Chromatography and Image Analysis," *J. Lipid Res.* 38:1482-1489.

She, Q-B. et al. (Feb. 1995). "Alteration in the Phosphatidylcholine Biosynthesis of Rat Liver Microsomes Caused by Vitamin $B_6$ Deficiency," *Biosci. Biotechnol. Biochem.* 59:163-167.

Tessitore, L. et al. (1999). "Expression of Phosphatidylethanolamine *N*-methyltransferase in Yoshida Ascites Hepatoma Cells and the Livers of Host Rats," *Carcinogenesis* 20(4):561-567.

Tijburg, L.B.M. et al. (Jul. 17, 1989). "Regulation of the Biosynthesis of Triacylgycerol, Phosphatidylcholine and Phosphatidylethanolamine in the Liver," *Biochim. Biophys. Acta* 1004(1):1-19.

U.S. Appl. No. 60/424,949, filed Nov. 11, 2002 for Watkins, 43 pages.

Vance, D.E. et al. (1988). "The Methylation of Phosphatidylethanolamine," *Prog. Lipid Res.* 27(1):61-79.

Vance, D.E. et al. (Apr. 1998). "Roles for the Methylation of Phosphatidylethanolamine," *Curr. Opin. Lipidol.* 9(2):125-130.

Waite, K.A. et al. (2002). "Choline Deficiency-induced Liver Damage is Reversible in Pemt Mice," *J. Nutr.* 132:68-71.

Walkey, C.J. et al. (1996). "Characterization of the Murine Phosphatidylethanolamine *N*-methyltransferase-2 Gene," *J. Lipid Res.* 37:2341-2350.

Walkey, C.J. et al. (Oct. 16, 1998). "Biochemical and Evolutionary Signifiance of Phospholipid Methylation," *J. Biol. Chem.* 273(42):27043-27046.

Watkins, S. (Mar. 2001). "Unique Phospholipid Metabolism in Mouse Heart in Response to Dietary Docosahexaenoic or Alpha-Linolenic Acids," *Lipids* 36(3):247-254.

Watkins, S. et al. (2002). "Unsaturated Fatty Acids," *Food and Science Technology* 117:559-588.

Watkins, S.M. et al. (2002). "Lipid Metabolome-wide Effects of the PPARγ Agonist Rosiglitazone," *J. Lipid Res.* 43:1809-1817.

Watkins, S.M. et al. (2003). "Phosphatidylethanolamine-*N*-methyltransferase Activity and Dietary Choline Regulate Liver-Plasma Lipid Flux and Essential Fatty Acid Metabolism in Mice," *J. Nutr.* 133:3386-3391.

Yao, Z et al. (Jul. 5, 1989). "Head Group Specificity in the Requirement of Phosphatidylcholine Biosynthesis for Very Low Density Lipoprotein Secretion from Cultured Hepatocytes," *J. Biol. Chem.* 264(19):11373-11380.

Yao, Z. et al. (Feb. 1990). "Reduction in VLDL, but not HDL, in Plasma of Rats Deficient in Choline," *Biochem. Cell Biol.* 68(2):552-558.

Yao, Z. et al. (Feb. 25, 1988). "The Active Synthesis of Phosphatidylcholine is Required for Very Low Density Lipoprotein Secretion from Rat Hepatocytes," *J. Biol. Chem.* 263(6):2998-3004.

Anonymous. (date unknown). Data located at <http://brenda.biobase.de/php/flat_result.php4?econ=2.1.1.17&organism_list+&Suchword=>, last visited Aug. 7, 2007, 24 pages.

* cited by examiner

METHODS OF DETERMINING CONTRIBUTIONS TO METABOLIC PATHWAYS

RELATED APPLICATIONS

The present application is a continuation of U.S. application Ser. No. 10/615,966, filed Jul. 9, 2003 now abandoned, which is a continuation of U.S. application Ser. No. 10/383,671, filed Mar. 7, 2003 now abandoned, which claims priority under 35 U.S.C. §119(e) from provisional application Nos. 60/363,587, filed Mar. 11, 2002, 60/373,912, filed Apr. 19, 2002, 60/401,684, filed Aug. 6, 2002, 60/424,949, filed Nov. 8, 2002, and 60/436,192, filed Dec. 24, 2002. The disclosures of U.S. application Ser. No. 10/615,966, filed Jul. 9, 2003, are hereby incorporated by reference herein in their entirety.

FIELD OF THE INVENTION

This invention relates generally to the field of assessing and monitoring metabolic processes, especially biosynthesis of lipid metabolites.

BACKGROUND OF THE INVENTION

Metabolites are synthesized and regulated by various metabolic processes and pathways. Each metabolite and its metabolic pathways are inevitably involved in certain biological processes of a system, e.g., human and could play an important role in a system's function and regulation. Therefore, it is useful to understand how metabolites, e.g., lipid metabolites are regulated by their biosynthesis pathways. There is a great need in the field to develop various ways to assess metabolic processes or pathways, e.g., measure contributions of pathways to metabolite productions.

SUMMARY OF THE INVENTION

The present invention is based, in part, on the discovery that levels of metabolite precursors, for each pathway can be used to determine each pathway's contribution to a metabolite production. Accordingly, the present invention provides methods for determining the contribution of a pathway to the biosynthesis of a metabolite, e.g., lipid class and databases or metabolite profiles generated therefrom.

In one embodiment, the present invention provides a method for determining the contribution of a pathway to the biosynthesis of a lipid class. The method includes determining the level of a marker composition in a precursor, determining the level of the marker composition in a lipid class, wherein the precursor is transformed to the lipid class via a pathway, and wherein the level of the marker composition in the precursor relative to the level of the marker composition in the lipid class is indicative of the contribution of the pathway to the biosynthesis of the lipid class.

In another embodiment, the present invention provides a method of determining the contribution of a first pathway and a second pathway to the biosynthesis of a lipid class. The method includes determining P1, wherein P1 is the level of a marker composition in a first precursor of a lipid class, wherein the first precursor is transformed to the lipid class via the first pathway, determining P2, wherein P2 is the level of the marker composition in a second precursor of the lipid class, wherein the second precursor is transformed to the lipid class via the second pathway, determining TL, wherein TL is the level of the marker composition in the lipid class, wherein the contribution of the first pathway is represented by (TL−P2)/(P1−P2) and the contribution of the second pathway is represented by (TL−P1)/(P2−P1).

In yet another embodiment, the present invention provides a method of providing a service. The method includes providing a signal identifying the contribution of a pathway to the biosynthesis of a lipid class in a sample as determined by the method provided by the present invention.

In still another embodiment, the present invention provides a method of providing a service. The method includes providing a signal identifying the contribution of a first pathway or second pathway or both to the biosynthesis of a lipid class in a sample as determined by the method provided by the present invention.

In another embodiment, the present invention provides a database which includes one or more signals, wherein each signal identifies the contribution of a pathway to the biosynthesis of a lipid class in a sample as determined by the method provided by the present invention.

In yet another embodiment, the present invention provides a database which includes one or more signals; wherein each signal identifies the contribution of a first pathway or a second pathway or both to the biosynthesis of a lipid class in a sample as determined by the method provided by the present invention.

In another embodiment, the present invention provides a method of providing a service. The method includes analyzing the database of the present invention and providing a signal identifying a profile corresponding to a characteristic of a sample in the database, wherein the profile comprises the contribution of at least one pathway to at least one lipid class.

In another embodiment, the present invention provides a method of determining the level of a marker composition of phosphatidylcholine in liver. The method includes determining the level of the marker composition of phosphatidylcholine in plasma.

In yet another embodiment, the present invention provides a method of determining the activity of phosphatidylethanolamine-N-methyltransferase (PEMT) pathway in a system. The method includes determining the level of 20:4n6 or 22:6n3 in the system.

In another embodiment, the present invention provides a method of identifying a diagnostic marker for a condition. The method includes determining the contribution of a pathway to the biosynthesis of a lipid class according to the method provided by the present invention in a sample from normal condition and a sample from said condition, wherein a variation in the contribution of the pathway associated with the sample from said condition, but not associated with the sample from the normal condition is indicative that the contribution of the pathway to the biosynthesis of the lipid class is a diagnostic marker for said condition.

In yet another embodiment, the present invention provides a method for determining the contribution of Acyl-CoA:cholesterol acyltransferase (ACAT) to the biosynthesis of cholesterol ester in plasma. The method includes determining a relative level, wherein the relative level is the level of a saturated fatty acid in cholesterol ester from plasma relative to the level of the saturated fatty acid in cholesterol ester from liver and wherein the relative level is indicative of the contribution of ACAT to the biosynthesis of cholesterol ester in plasma.

DESCRIPTION OF THE PREFERRED EMBODIMENTS

The present invention is based, in part, on the discovery that levels of metabolite precursors for each biosynthesis pathway can be used to determine each pathway's contribution to a metabolite production.

According to the present invention, one can choose a marker composition to track a desired metabolite precursor's contribution to a product's biosynthesis or track the pathway or enzyme activity transforming the desired metabolite precursor to a product. For example, the level of a marker composition in a precursor relative to the level of the marker composition in the product associated with the precursor is indicative of the contribution of the pathway or pathway activity converting the precursor to the product.

A marker composition can be any composition that is uniquely or characteristically associated with a pathway or enzyme activity or is stable and relatively unchanged throughout the biosynthesis of a product. In one embodiment, a marker composition can be one or more fatty acids, e.g., saturated fatty acids at SN-1 position of a metabolite, e.g., lipid class. For example, the marker composition can be 18:0 or 16:0 at SN-1 position of a fatty acid. In another embodiment, a marker composition can be one or more fatty acids at SN-1 or SN-2 position of a lipid class that are stable and relatively unchanged from the precursor stage to the product stage. Examples of such fatty acid include, without any limitation, 16:0, 18:0, 18:1, 18:2, 20:4 (20:4n6), and 22:6 (22:6n3).

In yet another embodiment, a marker composition can be one or more fatty acids that are characteristically or uniquely associated with a particular pathway for a precursor, but not significantly associated with other pathways for other precursors of the product. For example, 16:0 is particularly enriched in the precursor of CDP-choline pathway for the biosynthesis of phosphatidylcholine (PC) while 18:0, 22:6n3, and 20:4n6 are particularly enriched in the precursor of the phosphatidylethanolamine-N-methyltransferase (PEMT) pathway for the biosynthesis of PC.

Saturated fatty acids and monounsaturated fatty acids, e.g., 16:0, 16:1n7, and 18:0 are esterified to cholesterol by Acyl-CoA:cholesterol acyltransferase (ACAT) while polyunsaturated fatty acids, e.g., 20:4n6, 20:5n3, and 22:6n3 are esterified to cholesterol by lecithin:cholesterol acyltransferase (LCAT). In addition, 18:0, 22:6n3, and 20:4n6 are characteristically associated with the precursors of phosphatidylserine decarboxylase pathway for the biosynthesis of phosphatidylethanolamine (PE) while 16:0, 18:1, and 18:2n6 are characteristically associated with the precursors of CDP-ethanolamine pathway for the biosynthesis of PE.

In still another embodiment, a marker composition of 18:0, 16:0, or the ratio of 18:0 to 16:0 is used for the biosynthesis of PC, PE, diacylglyceride, triacylglyceride, 1,acyl-monoacylglyceride 3,phosphate, cholesterol ester, phosphatidic acid, cardiolipin, phosphatidylinositol, phosphatidylserine, and lysophospholipid.

The level of a marker composition usually can be the concentration of the marker composition, the level of the marker composition normalized against its corresponding class, e.g., total fatty acids, or the ratio of two or more fatty acids within the marker composition. For example, the level of a marker composition can be the level of 16:0, 18:0, 18:1, 18:2, 20:4n6, or 22:6n3 normalized against the total amount of fatty acids in the class. Alternatively the level of a marker composition can be represented by the ratio of any two, three, four, five, or six of 16:0, 18:0, 18:1, 18:2, 20:4n6, and 22:6n3.

In one embodiment, the level of a marker composition is the level of 18:0 or 16:0. In another embodiment, the level of a marker composition is the ratio of 18:0 to 16:0. In yet another embodiment, the level of a marker composition is the level of 18:1, 18:2, 20:4, or 22:6. In still another embodiment, the level of a marker composition is the ratio of any two, three, or four of 18:1, 18:2, 20:4 and 22:6.

The level of a marker composition can be determined by any suitable means. For example, the level of a marker composition for a precursor or a product can be determined by gas chromatography, high performance chromatography nuclear magnetic resonance, mass spectrometry, immunoassay, thin-layer chromatography, etc.

According to the present invention, the level of a marker composition in a precursor relative to the level of the marker composition in a product associated with the precursor can be used to assess the biosynthesis of a variety of metabolites, e.g., lipids. Examples of various pathways whose contribution to the biosynthesis of a metabolite can be monitored or measured using such relative level includes, without any limitation, phosphatidylethanolamone-N-methyltransferase (PEMT) pathway, CDP-choline pathway, phosphatidylserine decarboxylase (PSDC) pathway, CDP-ethanolamine pathway, diacylglyceride acyltransferase (DGAT) pathway, monoacylglyceride acyltransferase (MGAT) pathway, glycerolphosphate acyltransferase (GPAT) pathway, Acyl-CoA:cholesterol acyltransferase (ACAT) pathway, lecithin:cholesterol acyltransferase (LCAT) pathway, phospholipase C pathway, phospholipase D pathway, lipoprotein lipase, hormone-sensitive lipase, hepatic lipase and other lipases, cardiolipin synthase, phosphatidylinositol synthase, phosphatidylserine synthase, and phospholipase A2.

Examples of various lipid classes whose biosynthesis can be analyzed using such relative level include, without any limitation, phosphatidylcholine, phosphatidylethanolamine, cholesterol ester, phosphatidylserine, phosphatidylinositol, cardiolipin, triacylglyceride, diacylglyceride, phosphatidic acid, free fatty acid, sphingomyelin, phosphatidylglycerol, lysophospholipid, and 1,acyl-monoacylglyceride 3,phosphate.

In one embodiment, the level of a marker composition in a precursor relative to the level of the marker composition in a product associated with the precursor can be used to assess pathways or activities substantially associated with a particular marker composition in a product. For example, with respect to phosphatidylcholine production, most of 18:0, 20:4n6, and 22:6n3 are derived from PEMT pathway while most of 16:0 is derived from CDP-choline pathway. With respect to cholesterol ester production, most of saturated and monounsaturated fatty acids, e.g., 16:0, 16:1n7, and 18:0 are derived from ACAT pathway while most polyunsaturated fatty acids, e.g., 20:4n6, 20:5n3, and 22:6n3 are derived from LCAT pathway. In addition, with respect to phosphatidylethanolamine production, most of 16:0, 18:1 n9, and 18:2n6 are derived from the CDP-choline pathway while most of 18:0, 20:4n6, and 22:6n3 are derived from the phosphatidylserine decarboxylase activity.

In another embodiment, the level of a marker composition in a precursor relative to the level of the marker composition in a product associated with the precursor can be used to assess the contribution of PEMT pathway to the biosynthesis of phosphatidylcholine, the contribution of CDP-choline pathway to the biosynthesis of phosphatidylcholine, the contribution of PSDC pathway to the biosynthesis of phosphatidylethanolamine, the contribution of CDP-ethanolamine pathway to the biosynthesis of phosphatidylethanolamine, the contribution of ACAT pathway to the biosynthesis of cholesterol ester, the contribution of LCAT pathway to the biosynthesis of cholesterol ester, the contribution of DGAT pathway to the biosynthesis of diacylglyceride, the contribution of MGAT pathway to the biosynthesis of diacylglyceride, the contribution of GPAT pathway to the biosynthesis of 1,acyl-monoacylglyceride 3,phosphate, the contribution of phospholipase C or D pathway to the biosynthesis of phosphotidic acid, the contribution of lipoprotein lipase, hormone-sensitive lipase, hepatic lipase, or any other lipase pathway to the biosynthesis of diacylglyceride, the contribution of cardiolipin synthase to the biosynthesis of cardiolipin, the contribution of phosphatidylinosital synthase to the biosynthesis of phosphatidylinositol, the contribution of phosphatidylserine synthase to the biosynthesis of phosphatidylserine, and the contribution of phospholipase A2 to the biosynthesis of lysophospholipid.

In general, for the biosynthesis of phosphatidylcholine the marker composition of the precursor for the PEMT pathway can be the marker composition of phosphatidylethanolamine while the marker composition of the precursor for the CDP-choline pathway can be the marker composition of diacylglycerid, phosphatidic acid, or triacylglyceride. With respect to the biosynthesis of phosphatidylethanolamine, usually the marker composition of the precursor for the PSDC pathway can be the marker composition of phosphatidylserine while the marker composition of the precursor for the CDP-ethanolamine pathway can be the marker composition of 1,2-diacylglyceride, triacylglyceride, or phosphatidic acid.

With respect to the biosynthesis of cholesterol ester, the precursors for LCAT usually are fatty acids on the SN-2 position of plasma phospholipids and for ACAT usually are fatty acid CoA esters in liver. For example, saturated and monosaturated fatty acids such as 16:0, 16:1n7, and 18:0 are usually precursors for ACAT while polyunsaturated fatty acids such as 20:4n6, 20:5n3, and 20:6n3 are usually precursors for LCAT; and 18:2n6 serves as a precursor for both the ACAT and LCAT pathways. In one embodiment, the ACAT pathway activity can be represented by the biosynthesis of cholesterol ester in liver while the LCAT pathway activity can be represented by the difference between the plasma and liver cholesterol ester marker composition.

According to another aspect of the invention, the contribution of a pathway to the biosynthesis of a product can also be assessed by determining the product level and the precursor levels of two or more pathways involved in the biosynthesis of the same product. For example for a lipid biosynthesis comprising two pathways, one can determine the contribution of each pathway by determining the level of a marker composition in the precursor used by the first pathway (P1), the level of the marker composition in the precursor used by the second pathway (P2), and the level of the marker composition in the lipid class (TL). The contribution of each pathway can be determined by mathematical equations according to the general principal that marker compositions in precursors are relatively stable and unmodified during the biosynthesis of the product from the precursors.

For example, in a biosynthesis comprising two pathways, the contribution of the first pathway (C1) can be represented by (TL−P2)/(P1−P2) while the contribution of the second pathway (C2) can be represented by (TL−P1)/(P2−P1), both of which are obtained based on equations I and II as the following:

$$C1+C2=1 \quad (I)$$

$$C1 \times P1 + C2 \times P2 = TL \quad (II).$$

Usually, when the biosynthesis of a product contains more than two pathways, more than one marker composition could be used and the contribution of each pathway can be readily obtained according to the general principals described by equations I and II. In general, the equations provided by the present invention representing the contributions of two or more pathways can be further modified by a constant or conversion factor.

In one embodiment, the product is phosphatidylcholine, the first pathway is PEMT pathway using phosphatidylethanolamine as precursor, and the second pathway is CDP-choline pathway using diacylglyceride, phosphatidic acid, or triacylglyceride as precursor. In another embodiment, the product is phosphatidylethanolamine, the first pathway is PSDC using phosphatidylserine as precursor, and the second pathway is CDP-ethanolamine pathway using 1,2-diacylglyceride, triacylglycerid, or phosphatidic acid as precursor.

The contributions of various pathways as determined by the methods provided by the present invention can be relative contributions or quantified contributions. For example, the contribution of a pathway, e.g., PEMT to the biosynthesis of a lipid, e.g., phosphatidylcholine can be a percentage contribution or a contribution in quantitative amount, e.g. determined by the percentage contribution and the concentration of the lipid class.

The methods provided by the present invention for measuring the contribution of a pathway to the biosynthesis of a metabolite can be used to assess metabolite production in various conditions and from various sources. For example, the methods provided by the present invention can be used to analyze the biosynthesis of metabolites, e.g., lipids in vivo or in vitro. In one embodiment, the methods provided by the present invention can be used to analyze the lipids in various tissues including, without any limitation, liver, brain, heart, mammary gland, intestine, plasma, kidney, and pancreas.

According to one embodiment of the present invention, the level of a marker composition for phosphatidylcholine, triacylglyceride, or phophatidylethanolamine in plasma is representative of the level of a marker composition for phosphatidylcholine, triacylglyceride, or phosphatidylethanolamine in liver, respectively. In another embodiment of the present invention, the level of 20:4n6 or 22:6n3, e.g., in plasma is representative of the level of PEMT pathway activity, e.g., in liver.

According to another embodiment of the present invention, the level of a marker fatty acid in cholesterol ester in plasma relative to the level of the marker fatty acid in cholesterol ester in liver is representative of the contribution of Acyl-CoA: cholesterol acyltransferase (ACAT) to the biosynthesis of cholesterol ester in plasma. A marker fatty acid can be any fatty acid that are substantially the substrate for ACAT, but not LCAT. For example, most saturated fatty acids or monounsaturated fatty acids are substrates for ACAT while most polyunsaturated fatty acids are substrates for LCAT. In one embodiment, the concentration of a saturated fatty acid, e.g., 16:0 in cholesterol ester in plasma and liver is used to determine the percentage contribution of ACAT, and thus LCAT to the total cholesterol ester concentration of plasma.

According to the present invention, the composition of cholesterol ester in liver is derived substantially from ACAT pathway and the total composition of cholesterol ester in plasma is the sum total of cholesterol ester produced via ACAT pathway and exported to plasma and cholesterol ester produced via LCAT in plasma. Therefore, the contribution of ACAT pathway can be determined by determining the dilution of the marker fatty acid of the present invention in the plasma cholesterol ester whereas the contribution of LCAT pathway corresponds to the sum total of cholesterol ester produced excluding the contribution of ACAT pathway.

According to the present invention, methods for analyzing the biosynthesis of a metabolite as provided by the present invention have various applications in areas such as bioinformatics, therapeutics or diagnostics. In one embodiment, methods provided by the present invention can be used to provide services to an entity. For example, one can receive samples from a requesting party or obtain samples designated by a requesting party, analyze the contribution of one or more pathways to one or more metabolites in these samples according to the methods provided by the present invention, and provide the relevant results back to the requesting party, e.g., as electronic signals or computer readable form via any suitable means, e.g., internet, intranet, or wireless connection. Optionally one can provide an analysis of the results for the requesting party, e.g., searching the result database to identify any correlation between a characteristic of a sample, e.g., an abnormal or testing condition of a sample and the contribution pattern of one or more pathways to one or more metabolites.

In another embodiment, methods provided by the present invention can be used to build a database containing information of biosynthesis analyses, e.g., contribution of one or more pathways to one or more metabolites as part or all of the metabolic profile for a subject, e.g., human.

Usually the database provides one or more signals, outputs, or data points, each of which identifying contribution of a pathway to a metabolite corresponding to a subject under a condition. The subject can be any biosystem including, without any limitation, animals, humans, etc. or the samples thereof. The condition can be any suitable condition, e.g., one or more abnormal conditions, treatment of one or more therapeutic agent or testing agents, dietary conditions, various physiological conditions, etc. The database can be in any form that is accessible to a user. For example, the database can be in a computer readable form or accessible by a remote location or a predetermined entity, e.g., via internet, intranet, or wireless connection. In one embodiment, the database is searchable for any correlation between one or more predetermined conditions, e.g., a subject with a disease condition and the contribution pattern of one or more pathways to one or more metabolite productions.

In yet another embodiment, the methods provided by the present invention can be used to identify targets for therapeutic treatments or markers for diagnostics. Any contribution pattern of one or more pathways that is associated with an abnormal condition, but not with a normal condition, can be used at a diagnostic marker for the abnormal condition and/or a target for the treatment of the abnormal condition.

For example, one can identify a diagnostic marker by comparing the contribution pattern of a pathway between a normal condition and a known abnormal condition, e.g., a known disease or sub-optimal condition and identify contribution patterns that are hallmarks for the known abnormal condition, thus identify diagnostic markers for the known abnormal condition. In one embodiment, one can determine the contribution of one or more pathways to the biosynthesis of one or more lipid classes according to the methods provided by the present invention in a sample from normal condition and a sample from a known abnormal condition. Any variation in the contribution of the pathways that is significantly associated with the known abnormal condition, but not with the normal condition is indicative that the varied contribution pattern of the pathways can be used as a diagnostic marker for the known abnormal condition, e.g., a testing subject having the varied contribution pattern of the pathways is having the known abnormal condition.

EXAMPLES

The following examples are intended to illustrate but not to limit the invention in any manner, shape, or form, either explicitly or implicitly. While they are typical of those that might be used, other procedures, methodologies, or techniques known to those skilled in the art may alternatively be used.

Symbols used in the examples:

IV: Liver
PLA: Plasma
ADP: Adipose
HRT: Heart
MUS: Muscle
PC: Phosphatidylcholine
PE: Phosphatidylethanolamine
PS: Phosphatidylserine
PA: Phosphatidic Acid
TG: Triacylglyceride
CE: Cholesterol Ester
FS: Free Sterol
DG: 1,2-Diacylglyceride
FA: Free Fatty Acid
SP: Sphingomyelin
CL: Cardiolipin Hence, the symbol LIVPC16:0 denotes the concentration of 16:0 in liver phosphatidylcholine (expressed in nMoles per g). The symbol % LIVPC16:0 indicates the mole percentage concentration of 16:0 in liver phosphatidylcholine (expressed as a percentage of the total amount of fatty acids in liver phosphatidylcholine).

The composition of each lipid class is highly regulated, and changes in the concentration of certain fatty acids within a lipid class can be used to determine which pathway is responsible for the production of that lipid class. The primary mathematical approach used herein is a solver equation, whereby the concentration of a given fatty acid within the two or more precursor lipid classes, and the concentration of that fatty acid in the product lipid class, are used to estimate the relative flux through the two enzyme systems that modify substrate into product.

Other approaches can be used, some of these may resemble regression analyses or other statistical techniques. The absolute concentration of the product lipid class can be used to estimate the steady state contribution of each contributing metabolic pathway to the concentration in the product lipid class.

The solver or regression approach described herein relies on using accurate substrate and/or product composition data to calculate the flux of the enzyme pathway(s) contributing to the measured class(es). Ideally, the quantitative concentration of each lipid class can be used to scale the assay to calculate the absolute concentration or amount of the lipid class synthesized via a given pathway. A solver approach takes (1) the concentration of a fatty acid in each of the two (or more, if there are more pathways present) possible precursors and (2) the concentration of that same fatty acid in the product, and (3) determines the percent contribution of each of the two pathways to the production of that product.

Example 1

Analysis of Phosphatidylcholine Production

Phosphatidylcholine is primarily synthesized via one of two pathways, the PEMT pathway and the CDP-choline pathway. The CDP-choline pathway synthesizes phosphatidylcholine from diacylglyceride and phosphocholine, and the PEMT pathway synthesizes phosphatidylcholine from phosphatidylethanolamine and S-adenosylmethionine. (Reo et al., *Biochim Biophys Acta* 1580(23):171-188, 2002).

The relative contribution of each of these pathways to total liver phosphatidylcholine composition has been estimated by several groups. Reo et al. (2002) using radiolabeled choline and ethanolamine has determined that in rats approximately 70 percent of hepatic phosphatidylcholine was synthesized by the CDP-choline pathway and 30 percent was synthesized by the PEMT pathway. These results were generally in agreement with previous findings (references 4, 16-19 in Reo et al., 2002). Roy et al. (2002) additionally demonstrated that newly synthesized phosphatidylethanolamine is preferentially used for the PEMT reaction (the current solver approach may not provide true 0 and unity endpoints because of this phenomenon).

Kinetic analysis showed conversion of phosphatidylethanolamine to phosphatidylcholine occurred at three times the rate of diacylglyceride to phosphatidylcholine via the CDP-choline pathway (Reo et al., 2002). The CDP-choline pathway activity is dependent on choline status and the CDP-ethanolamine pathway is dependent on ethanolamine status. Therefore, it is possible to modulate both pathways via their respective substrate. The activation of these pathways takes place at the kinase step. Since choline kinase and ethanolamine kinase may be in fact the same enzyme, it is possible that choline and ethanolamine act as competitive inhibitors for the other pathway.

In the inventor's experience, phosphatidylethanolamine concentrations are usually found to be constant at around 8-10,000 nanomoles per gram in mouse liver, thus, it is believed that phosphatidylethanolamine synthesis and conversion to other glycerolipid classes is highly regulated. The metabolic mechanisms by which phosphatidylethanolamine concentrations can be maintained include it's biosynthesis via phosphatidylserine decarboxylase and CDP-ethanolamine pathways, and its degradation or conversion to other glycerolipid classes by PEMT or phospholipase activity.

The PEMT gene gives rise to two enzymatic isoforms, PEMT1 and PEMT2. PEMT1 activity is present in the endoplastic reticulum and is likely the isoform involved in lipoprotein export and PEMT2 activity is found in the mitochondria. There are some data to suggest that the second form of PEMT is involved in cell proliferation and potentially cancer (see, e.g., Tessitore et al., *Carcinogenesis* 20(4):561-567, 1999).

The fatty acid composition of phosphatidylcholine produced via the CDP-choline pathway in the PEMT pathway has been studied by DeLong et al. (*J Biol Chem.* 274(42): 29683-29688, 1999). Phosphatidylcholine species produced via the CDP-choline pathway "were mainly comprised of median chain, saturated (e.g., 16:0/18:0) species. On the other hand, PC molecules from the PE methylation pathway contain a higher percentage of arachidonic and were more diverse than those from the CDP: choline pathway."

An analysis of the data from the DeLong et al. (1999) paper show that 16:0, 18:2, 18:1 and 20:4 are the predominant fatty acids of phosphatidylcholine produced via the CDP-choline pathway. In contrast, 18:0, 20:4, 16:0, 18:1, and 18:2 were the predominant fatty acids produced via the PEMT pathway. The inventor believes that 20:4 could play an important role in intercellular signaling and PEMT could have a role in generating lipids active in cellular regulation. The authors of DeLong et al. do not identify 22:6 as a hallmark fatty acid of PEMT activity, despite its presence in phosphatidylcholine (although in low concentrations) in this study.

It is the discovery of the present invention that 18:0, 20:4, and 22:6 are hallmark fatty acids of phosphatidylcholine produced via the PEMT pathway, while 16:0, 18:1, and 18:2 are hallmark fatty acids of the CDP-choline pathway. While it is useful for many assays to have a marker for one of the two pathways that is unique, the solver approach described herein utilizes the composition of the precursors to phosphatidylcholine to determine the relative flux through each of two main phosphatidylcholine biosynthesis pathways.

In particular, this analysis takes advantage of the fact that it is reasonable to assume that the 16:0 and 18:0 present in phosphatidylcholine is on the SN-1 position, and that this position is stable and not remodeled by phospholipase after the conversion of phosphatidylethanolamine and diacylglyceride to phosphatidylcholine. Thus, by knowing the composition of the SN-1 position of phosphatidylcholine and its precursors, the percent contribution of each of the two precursors to phosphatidylcholine concentrations can be calculated using the methods described herein.

Because phosphatidylcholine is synthesized by the modification of the head groups of 1,2-diacylglyceride (1,2-DAG) or phosphatidylethanolamine (PE) by the CDP-choline or PEMT pathways, respectively (meaning the fatty acid composition of these precursors is not altered by the reactions themselves), and because 1,2-DAG and PE have unique fatty acid compositions, the proportion of PC synthesized from either 1,2-DAG or PE can be calculated from the fatty acid composition of the precursors and PC.

In particular, the saturated fatty acid composition of PC and its precursors is thought to be useful because of a relatively constant biological property of phospholipids. Phospholipids contain almost exclusively saturated fatty acids at the SN-1 position (the first of their two hydroxyl groups available for fatty acid esterification), thus, the composition of phospholipids is approximately 50% saturated (it's typically close to 46%). Although the SN-1 position contains almost entirely saturated fatty acids, the chain length of the saturated fatty acid can vary, and each lipid class typically has a unique "standard" composition. The following table displays the means and standard deviations for the 16:0, 18:0 and total saturated fatty acid composition of the major liver lipids in mice:

| Lipid Class | % Saturated | % 16:0 | % 18:0 | Other Saturates |
|---|---|---|---|---|
| Phosphatidylcholine (PC) | 45.8 ± 1.7 | 33.4 ± 3.4 | 11.7 ± 2.9 | 0.7 ± 0.4 |
| Phosphatidylethanolamine (PE) | 40.6 ± 2.1 | 21.9 ± 1.6 | 18.1 ± 2.4 | 0.6 ± 0.3 |
| Phosphatidylserine (PS) | 47.3 ± 3.8 | 9.0 ± 1.9 | 37.0 ± 4.7 | 1.3 ± 0.7 |
| Diacylglyceride (DG) | 32.1 ± 5.5* | 23.6 ± 4.1 | 5.3 ± 1.7 | 3.2 ± 1.0 |
| Triacylglyceride (TG) | 30.8 ± 4.7* | 27.0 ± 4.6 | 2.2 ± 0.9 | 1.6 ± 0.5 |

*See below for why these lipids are comprised of less saturated fatty acids than their phospholipid analogues.

Using Fatty Acid Composition to Estimate Proportional Contribution of PEMT to Total PC Biosynthesis.

The 18:0 and 16:0 composition of phosphatidylcholine is indicative of the pathway from which phosphatidylcholine is synthesized. Generally, phosphatidylcholine with 16:0 in the SN-1 position is derived from the CDP-choline pathway and phosphatidylcholine with 18:0 in the SN-1 position is derived from the PEMT to pathway. Therefore the contribution from PEMT or CDP-choline pathway can be calculated based on the level of 16:0 and 18:0 in the precursors and the level of phosphatidylcholine.

To be more precise, the exact composition of diacylglyceride phosphatidylethanolamine, and phosphatidylcholine in a tissue can be used to calculate the relative flux of the PEMT and CDP-choline pathways. Specifically, the ratio of 18:0 to 16:0 in each of the precursors was determined and used to "solve" for the ratio of 18:0 to 16:0 in the PC product.

In general, one could 1) determine the fatty acid composition of phosphatidic acid or diacylglyceride, phosphatidylcholine, and phosphatidylethanolamine in liver, and 2) use the composition of the precursors of each of the two biosynthetic pathways and phosphatidylcholine to determine the relative contribution of each biosynthetic pathway to total phosphatidylcholine concentrations.

The calculation can be carried out as the following.

Values:
k1: percentage of PE going into PC
k2: percentage of PA going into PC
val_pe: PE (X)measured
val_pa; val_dag: PA or 1,2-DAG(X)measured
val_pc: PC (X)measured where X equals the concentration of 16:0 or 18:0 within the appropriate lipid class expressed as a percentage of total fatty acids within that class or is the ratio of the concentrations of 18:0 to 16:0 within the lipid class.

Constraints:

Set $k1+k2=1$ $(k1*\text{val}\_pe)+(k2*\text{val}\_pa)=\text{val}\_pc$

Results:
k1=Percentage contribution of PEMT pathway.
k2=Percentage contribution of CDP-choline pathway The following table is a screen capture of the Excel Datasheet used to calculate the percentage contribution of PEMT and CDP-choline to the synthesis of PC. Phosphatidic acid was used as a surrogate for 1,2-DAG, the precursor of the CDP-choline pathway. PA composition was calculated from the composition of TAG as described below. The table at the bottom right is the input box into which data from a sample is pasted.

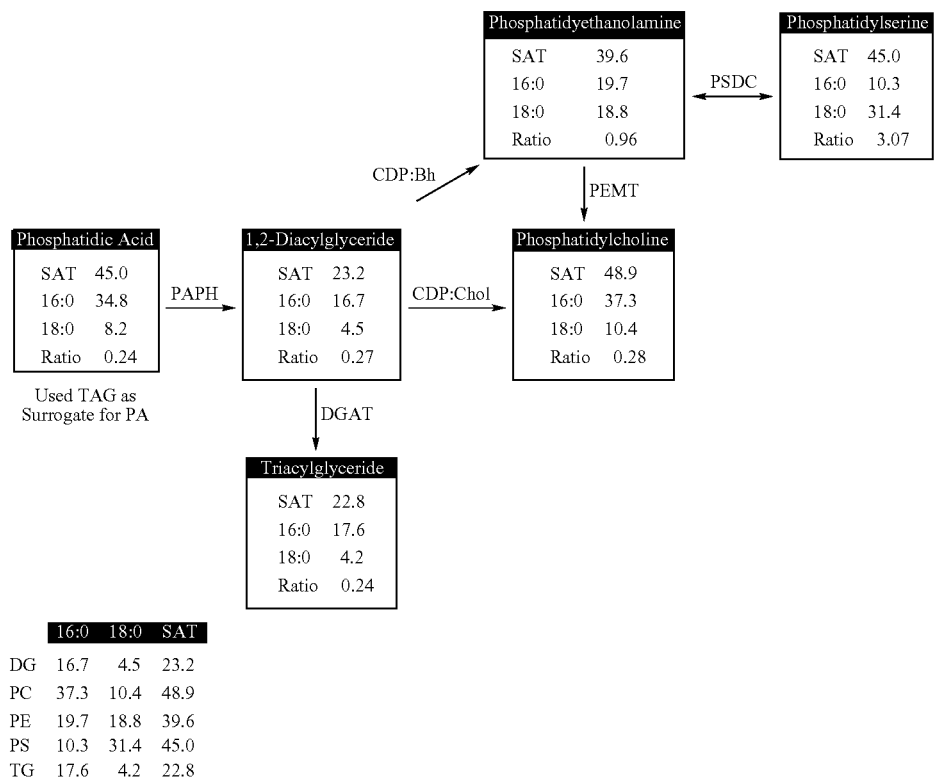

Several issues should be considered in calculating the activity of PEMT or CDP-choline pathway activity by using the composition of 1,2-DAG as the precursor for the CDP-choline pathway. First, the composition of 1,2-DAG, the direct precursor of PC via the CDP-choline reaction, is not always reflective of the PC precursor pool, because 1,2-DAG can be synthesized via two different pathways, with the second (non phosphatidic acid-derived) pathway often producing the majority of the 1,2-DAG. Therefore, the composition of phosphatidic acid can act as a surrogate for the appropriate 1,2-DAG, because it can be assumed to be the direct and only precursor to 1,2-DAG that will be converted to PC. A simple measurement of phosphatidic acid fatty acid composition will provide the appropriate data for the assay.

In addition, the composition of phosphatidic acid (PA) should be exactly reflective of the 1,2-DAG substrate available for conversion to PC, but the composition of PA could be difficult to measure at times. Therefore, the saturated fatty acid composition of TAG can act as a surrogate for the saturated fatty acid composition of PA because it's saturated fatty acids are in the SN-1 position and derived from the saturated fatty acids of PA. However, because TAG contains 3 fatty acids, rather than 2, and because the fatty acid that can be cleaved off to form 1,2-DAG is ostensibly random, the total content of saturated fatty acids must be normalized to ~45%, the putative content of phosphatidic acid.

For example, using TAG as a surrogate for PA, the calculation can be carried out as the following.

1. Calculating the composition of phosphatidic acid (PA):

Total saturated fatty acid composition of PA=0.45[1]

[1] The value 0.45 was chosen because it is typically the percent of total fatty acids comprised by saturates within phosphatidic acid. A number appropriate for the biological system under investigation should be used here.

Percentage of PA comprised by:

$16:0 = (TAG\% \ 16:0 * 0.45^1) / TAG\%_{Total\ Saturated\ FA\ Composition}$ val_pe: PE (ratio of 18:0 to 16:0)$_{measured}$ val_pa: PA (ratio of 18:0 to 16:0)$_{estimated\ from\ TAG}$ val_pc: PC (ratio of 18:0 to 16:0)$_{measured}$ Constraints:

Set $k1+k2=1$ $(k1*val\_pe)+(k2*val\_pa)=val\_pc$

Results:

k1=Percentage contribution of PEMT pathway k2=Percentage contribution of CDP-choline pathway The following table is a screen capture of the Excel Datasheet used to calculate the percentage contribution of PEMT and CDP-choline to the synthesis of PC. Phosphatidic acid was used as a surrogate for 1,2-DAG, the precursor of the CDP-choline pathway. PA composition was calculated from the composition of TAG as described above. The table at the bottom right is the input box into which data from a sample is pasted.

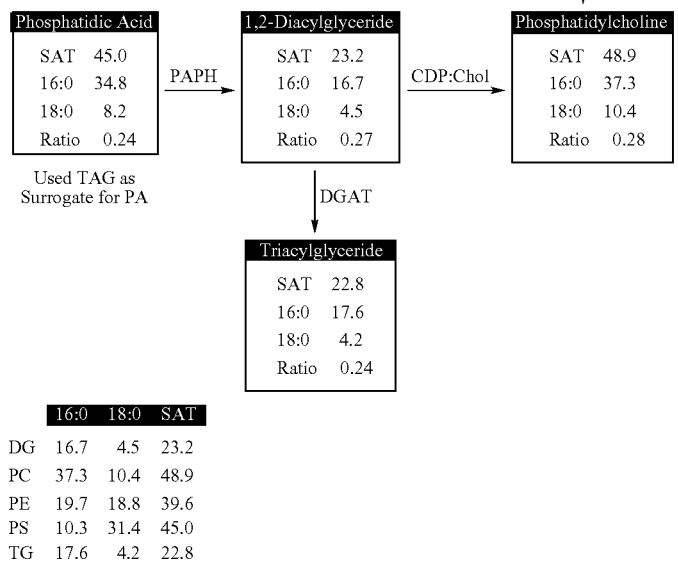

Percentage of PA comprised by:

$18:0 = (TAG\% \ 18:0 * 0.45^1) / TAG\%_{Total\ Saturated\ FA\ Composition}$

Ratio of 18:0 to 16:0 in PA is calculated from the above estimated values.

2. Solver Equation:

Values:

k1: percentage of PE going into PC k2: percentage of PA going into PC

Using Other Fatty Acids to Calculate Pathway Flux or to Estimate the Degree of Phosphatidylcholine Remodeling.

Using 16:0, 18:0 or the ratio 18:0 to 16:0 within each of the substrate and product lipid class to calculate pathway flux provides the most stable assay because these fatty acids are present at the SN-1 position of the phospholipids, and are not actively hydrolyzed by phospholipases.

Other fatty acids within phosphatidylcholine, diacylglycerides, and phosphatidylethanolamine can be plugged into these equations as well, even though these other fatty acids are present at the SN-2-position, which is more actively hydrolyzed by phospholipases in the process of remodeling. Thus, the degree of remodeling within phosphatidylcholine after its conversion from diacylglyceride or phosphatidylethanolamine can be calculated by comparing the unsaturated fatty acid composition of phosphatidylcholine with its precursors. Because the present method calculates the percentage contribution of each pathway to the total amount of phosphatidylcholine, the difference between the concentration of unsaturated fatty acids within phosphatidylcholine as measured, and as it is predicted by and the mixing of these two substrate pools can be assumed to be the degree of SN-2 position remodeling of phosphatidylcholine.

PEMT Assay in Liver

The following assay calculates the percentage of total liver phosphatidylcholine produced by PEMT.

$$x=(((\% LIVPC(y))-(\% LIVDG(y)))/(((\% LIVPE(y))-(\% LIVDG(y)))$$

Where: x=the percentage of total liver phosphatidylcholine produced by PEMT and: (y)=16:0, 18:0 or a ratio of the two.

In many cases, the liver DG may not be an acceptable component of this equation. For instance, if the majority of the DG in liver is produced by hydrolysis of triacylglyceride or phospholipid rather than by the hydrolysis of phosphatidic acid (de novo synthesis of 1,2-DG occurs by conversion of phosphatidic acid), then a surrogate for de novo synthesized DG should be used. Good surrogates include phosphatidic acid and triacylglycerides. If triacylglycerides are used in place of diacylglycerides in this equation, then the final mole percentage concentration of the metabolite (i.e. TG16:0) should be divided by 0.66 because diacylglycerides have ⅔rds the number of fatty acids per molecule as do triacylglycerides.

Equations using surrogates for 1,2-DG include:

$$x=((\% LIVPC(y))-(\% LIVPA(y)))/(((\% LIVPE(y))-(\% LIVPA(y)))$$

$$x=((\% LIVPC(y))-((\% LIVTG(y))/0.66))/(((\% LIVPE(y))-(\% LIVTG(y))/0.66))$$

Where: x=the percentage of total liver phosphatidylcholine produced by PEMT and: (y)=16:0, 18:0 or the ratio of the two.

Because phosphatidylcholine is synthesized by either the PEMT pathway or the CDP-choline, the percentage of liver phosphatidylcholine produced by the CDP-choline pathway can be calculated from the percentage of phosphatidylcholine produced by PEMT.

Percentage of liver phosphatidylcholine produced by the CDP-choline pathway:

$$z=1-x$$

Where z=the percentage of liver phosphatidylcholine produced by the CDP-choline pathway And: x=the percentage of liver phosphatidylcholine produced by the PEMT pathway The quantitative amount of phosphatidylcholine produced by each pathway can be calculated from these calculated values and the quantitative amount of phosphatidylcholine in the liver.

Quantitative amount of liver phosphatidylcholine produced by:

$$PEMT=x \text{ (see above)}*LIVPC\text{tot\_nmoles\_per\_g}$$

$$CDP\text{-Choline}=z \text{ (see above)}*LIVPC\text{tot\_nmoles\_per\_g}$$

The quantitative amount of PC produced by each pathway in tissues other than liver can be calculated in the same way.

The quantitative amount of PC produced by each pathway in plasma can be calculated in the same way.

Example 2

Analysis of Phosphatidylserine Decarboxylase/CDP-ethanolamine Pathways

Synopsis of Assay: The same assay protocol as described for the PEMT protocol can be used to determine the contribution of the phosphatidylserine decarboxylase and CDP-ethanolamine pathways to the biosynthesis of phosphatidylethanolamine. The 18:0 content of phosphatidylethanolamine is principally derived from phosphatidylcholine and 16:0 content of phosphatidylethanolamine is principally derived from diacylglyceride. Hence, 18:0 and 16:0 composition of diacylglyceride, phosphatidylethanolamine, and phosphatidylserine can be used to calculate the activities of phosphatidylserine decarboxylase and CDP-ethanolamine.

Other possible assays: Other fatty acids within phosphatidylserine and diacylglyceride may prove better indices of flux into phosphatidylethanolamine than 16:0 and 18:0. Examples include: 18:1, 18:2, 20:4, 22:6. Additionally, the total concentration of phosphatidylethanolamine is important and might be used to scale the actual flux of the two contributing pathways.

Example 3

Lecithin-Cholesterol Acyltransferase (LCAT)

Substrate. Fatty acids on the SN-2 position of phospholipids and free cholesterol Product: Cholesterol ester and lyso-phospholipid Location: Plasma, surface of HDL particles Function: To solubilize cholesterol in HDL core material for reverse transport of cholesterol from peripheral tissues back to liver.

Synopsis of assay: In general, saturated fatty acids and monounsaturated fatty acids are esterified to cholesterol by ACAT, and polyunsaturated fatty acids are esterified to cholesterol by LCAT. The exception is 18:2, which has complex incorporation pattern probably related to whether or not it is a dietary component. The relative contribution of ACAT and LCAT to plasma cholesterol ester concentrations can be determined by determining the saturated, monounsaturated, and polyunsaturated fatty acid composition of plasma cholesterol esters.

Additionally, if liver cholesterol esters are assayed in addition to plasma cholesterol esters, the composition of liver cholesterol esters can be assumed to represent the composition of cholesterol esters synthesized via ACAT, and the difference between the plasma and liver cholesterol ester composition can be assumed to be contributed by the activity of LCAT.

Furthermore, the composition difference between phosphatidylcholine and lysophosphatidylcholine can be used to indicate the fatty acids utilized by LCAT.

LCAT is one of two enzymes responsible for esterifying fatty acids to free cholesterol for plasma CE transport. The other enzyme, ACAT2, is present in the liver and is responsible for creating the CE that is sent into the blood in VLDL (forward cholesterol transport), eventually contributing to LDL cholesterol content. LCAT is presumed to be involved in "good" or reverse cholesterol transport by mediating the esterification and, thus, solubilization of free cholesterol from peripheral tissues, which causes it to migrate into the core of HDL particles.

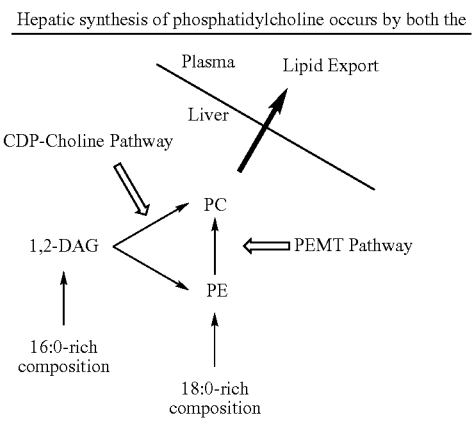

Hepatic synthesis of phosphatidylcholine occurs by both the

By plotting the composition of plasma CE against liver CE, it is clear that plasma CE contains significantly more 18:2n6 and 20:4n6 in both primates and mice while primates contain high concentrations of 20:5n3 in plasma CE and mice contain high concentrations of 22:6n3 in plasma CE. Liver CE is comprised of much higher concentrations of 16:0, 16:1n7 and 18:0 than plasma, while the plasma and liver 18:1n9 composition of CE is relatively equal. Thus a component of CE that is synthesized only by ACAT in the liver is the saturated fatty acid content of CE.

Dietary Oil Treated Primates

Plotting the plasma cholesterol ester composition against liver cholesterol ester composition can be used to determine selectivity for fatty acid by LCAT or ACAT. Plotting the saturated, monounsaturated (MUFA) and polyunsaturated fatty acids saturated fatty acids have a slope of less than 1, MUFA look like unity and polyunsaturated fatty acids have a slope >1. The only exception is polyunsaturated fatty acids from corn oil treated primates. These primates look like 18:2 is esterified to cholesterol ester by ACAT as well as LCAT. An important feature here is the polyunsaturated fatty acids from corn oil treated animals do not fall on the line for the polyunsaturated fatty acids for all other dietary oils.

Example 4

Analysis of Acyl-CoA Acyltransferase (ACAT2)

Overview of Assay: When both liver and plasma samples are available, the concentration of each fatty acid in cholesterol ester in plasma and liver can be used to determine the percentage contribution of ACAT and LCAT, respectively, to the total cholesterol ester concentration of plasma. This can be done because the composition of cholesterol ester in liver can be assumed to be derived exclusively from ACAT activity, and because the total composition of cholesterol ester in plasma must be the sum total of cholesterol ester produced via ACAT and exported to plasma, and cholesterol ester produced via LCAT in plasma. Hence, by knowing any single fatty acid that is substrate for ACAT and not LCAT, the contribution of ACAT to total plasma cholesterol ester concentrations can be calculated by calculating the dilution of the selected fatty acid in the plasma cholesterol ester pool.

Several assumptions are required for such calculation and the data selected for comparison preferably are compositional (mole percentage) data, not quantitative concentration data. Once the compositional data is used to determine the percentage contribution of ACAT and LCAT, respectively, to total plasma cholesterol ester concentrations, the quantitative concentration of cholesterol ester in plasma can be converted into the quantitative amount produced by ACAT and the quantitative amount produced by LCAT. Furthermore, the quantitative amount of cholesterol ester produced via ACAT can be compared to the cholesterol ester concentration in liver as an estimate of export efficiency in liver.

Assay Parameters

Knowns:
　Plasma CE composition
　Plasma CE concentration
　Liver CE composition
　Liver CE concentration.

Unknowns:
　Percentage of cholesterol ester derived from LCAT
　Percentage of cholesterol ester derived from ACAT
　Rate data for either ACAT or LCAT
　Quantitative flux to cholesterol ester between liver and plasma.

Assumptions:
　The fatty acid component of the plasma cholesterol ester used for the calculations is present on the cholesterol ester predominantly as the result of ACAT activity. In an LCAT knockout, plasma cholesterol ester composition would equal or be similar to liver cholesterol ester composition while in ACAT knockout, liver cholesterol ester concentrations would approach zero, and therefore plasma cholesterol ester composition would not equal liver cholesterol ester composition.

Analysis Process:

1) Selecting the fatty acid or fatty acids for use in the assay.

The first step in selecting the fatty acid or fatty acids for use in this assay is to plot to plasma cholesterol ester composition (expressed in mole percentage) against the liver cholesterol ester composition. The fatty acid selected must have a slope <1, because fatty acids with a slope >1 are present in plasma due principally to LCAT activity. It is important in this assay that the fatty acid selected be derived exclusively from ACAT activity because the assay relies on quantifying the dilution of that fatty acid in the plasma cholesterol ester composition relative to the liver cholesterol ester composition. Thus, the ideal fatty acid chosen for this assay will have a slope closer to zero than the one, and will be of a sufficiently high concentration in both liver and plasma cholesterol esters such that the signal derived from the analysis is reliable.

2) Select a fatty acid: presumed not to be substrate for LCAT, with a slope near zero, and with a sufficiently high concentration in liver cholesterol esters to provide a good signal for the assay. (The lowest slope and the highest concentration in liver both provide the best signal for the assay.)

3) Assemble the composition of liver and the composition of plasma and the absolute concentrations of cholesterol esters in liver in the absolute concentration of cholesterol esters in plasma.

4) Perform equations as described below to calculate the percentage of cholesterol esters produced by ACAT, the percentage of cholesterol esters produced by LCAT, the concentration of cholesterol esters derived from LCAT, the concentration of cholesterol esters derived from ACAT, in the ratio of cholesterol ester in plasma to cholesterol ester in liver. The equation is the following. If the total saturated fatty acid composition of cholesterol ester is chosen as the variable (as it is for mice, primates and humans, because LCAT does not make CE with a saturated fatty acid composition), then the equation would be plasma CE % SAT/Liver CE % SAT. This equation calculates the dilution of liver derived CE into plasm CE because the % SAT in CE produced by LCAT (in plasma) should be zero.

Metabolic Signatures

For all equations listed below, values for DG, PA or (TG/0.667) may be substituted for each other. $-(y)=16:0, 18:0,$ SAT or a ratio of two of these PEMT Pathway Assay measures the percentage of tissue phosphatidylcholine derived from PEMT $$PEMT=((\%\ LIVPC(y))-(\%\ LIVDG(y)))/((\%\ LIVPE(y))-(\%\ LIVDG(y)))$$

or $$=1-((\%\ LIVPC(y))-(\%\ LIVPE(y)))/((\%\ LIVDG(y))-(\%\ LIVPE(y)))$$

or $$=1-CDP\text{-}CT$$

CDP-Choline Pathway

Assay measures the percentage of tissue phosphatidylcholine derived from CDP-CT $$CDP\text{-}CT=((\%\ LIVPC(y))-(\%\ LIVPE(y)))/((\%\ LIVDG(y))-(\%\ LIVPE(y)))$$

or $$=1-((\%\ LIVPC(y))-((\%\ LIVDG(y)))/(((\%\ LIVPE(y))-(\%\ LIVTG(y)))$$

or $$=1-PEMT$$

Phosphatidylserine Decarboxylase (PSDC) Pathway

Assay measures the percentage of tissue phosphatidylethanolamine derived from PSDC $$PSDC=((\%\ LIVPE(y))-(\%\ LIVDG(y)))/((\%\ LIVPS(y))-(\%\ LIVDG(y)))$$

or $$=1-CDP\text{-}ET$$

or $$=1-((\%\ LIVPC(y))-(\%\ LIVPS(y)))/((\%\ LIVDG(y))-(\%\ LIVPS(y)))$$

CDP-Ethanolamine Pathway

Assay measures the percentage of tissue phosphatidylethanolamine derived from CDP-ET $$CDP\text{-}ET=((\%\ LIVPC(y))-(\%\ LIVPS(y)))/((\%\ LIVDG(y))-(\%\ LIVPS(y)))$$

or $$=1-PSDC$$

or $$=1-((\%\ LIVPE(y))-(\%\ LIVDG(y)))/((\%\ LIVPS(y))-(\%\ LIVDG(y)))$$

Acyl-CoA Acyltransferase 2 (ACAT2)

Assay measures the percentage of plasma cholesterol esters derived from ACAT2

$$ACAT2=(\%\ PLACESAT)/(\%\ LIVCESAT)$$

or $$=(\%\ PLACE16:0)/(\%\ LIVCE16:0)$$

Lecithin: Cholesterol Acyltransferase (LCAT)

Assay measures the percentage of plasma cholesterol esters derived from LCAT $$LCAT=1-ACAT2$$

or $$1-((\%\ PLACESAT)/(\%\ LIVCESAT))$$

Triacylglyceride Metabolism

De novo vs. recycling=(% $TGSAT$)/0.667

If value approximates 50%, then most TG is produced de novo

If value is lower than 50% then recycling of TG-DG is occurring.

PLC or PLD contributing to TG biosynthesis $$PLC/PLD=(\%\ TGPUFA)-(\%\ TG18:2n6)$$

If PLC/PLD increases after treatment there is an increase in PLC or PLD activity.

Check to see if TG composition reflects PE or PC to determine substrate for PLC or PLD Check to see if effect is consistent in DG and/or PA to determine if it is a PLC or a PLD Other Key Activities in Lipid Metabolism It is believed that the methods described herein can be adapted to study and characterize the following:

Diacylglyceride Acyltransferase (DGAT)
Lipoprotein Lipase (LPL)
Hormone-Sensitive Lipase (HSL)
Glycerol-3-Phosphate Acyltltransferase
Lyso-Phosphatidic Acid Acyltransferase (LPAT)
Dihydroxyacetone Phosphate Acyltransferase (DHAP-AT)
Hepatic Lipase
Cardiolipin Synthase
Phosphatidylinositol Synthase
Fatty acid Synthase
Delta-9 Desaturase
Delta-6 desaturase
Delta-5 Desaturase
Elongase Example 5

Assessing the Biosynthetic Origin of Phosphatidylcholine

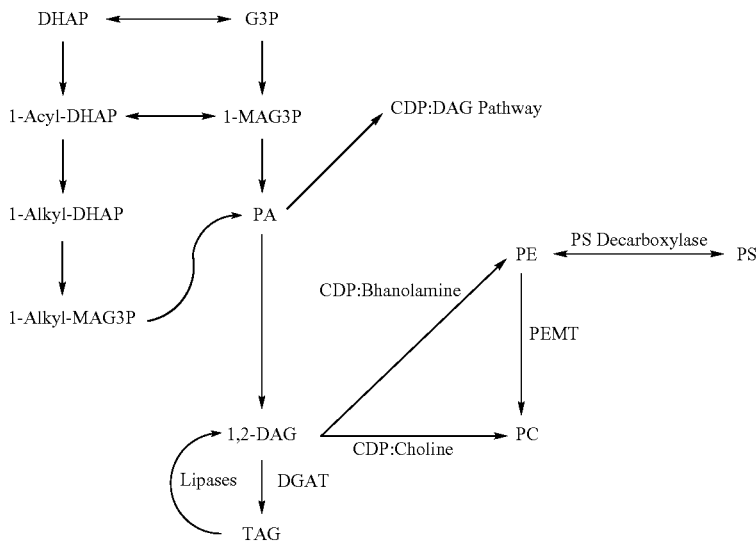

Liver Phosphatidylcholine Synthesis

Liver phosphatidylcholine (PC) is synthesized by two pathways: (1) the CDP-choline pathway and (2) the PEMT pathway. The CDP-choline pathway uses 1,2-DAG and CDP-choline as its substrate, while the PEMT pathway uses phosphatidylethanolamine and S-adenosylmethionine or S-adenosylhomocysteine as substrate. Both 1,2-DAG and phosphatidylethanolamine are acylated, meaning that they already contain the two fatty acids that will comprise the fatty acid composition of synthesized phosphatidylcholine once it is converted by the CDP-choline or PEMT pathway. Hence, unless newly synthesized phosphatidylcholine has its fatty acid composition remodeled, the composition of phosphatidylcholine should be a mixture of the fatty acid composition of phosphatidylethanolamine and 1,2-DAG.

Liver Phosphatidylethanolamine Synthesis

Liver phosphatidylethanolamine (PE) is synthesized by two pathways: (1) the CDP-ethanolamine pathway and (2) the phosphatidylserine decarboxylase pathway. The CDP-ethanolamine pathway uses 1,2-DAG and CDP-ethanolamine as its substrate, while the phosphatidylserine decarboxylase pathway uses phosphatidylserine as substrate. Both 1,2-DAG and phosphatidylserine are acylated, meaning that they already contain the two fatty acids that will comprise the fatty acid composition of synthesized phosphatidylethanolamine once it is converted by the CDP-ethanolamine or the phosphatidylserine decarboxylase pathway. Hence, unless newly synthesized phosphatidylethanolamine has its fatty acid composition remodeled, the composition of phosphatidylethanolamine should be a mixture of the fatty acid composition of phosphatidylserine and 1,2-DAG.

Liver 1,2-diacylglyceride Synthesis

Liver 1,2-diacylglyceride (DAG) is synthesized de novo from phosphatidic acid. Like PC and PE, DAG is synthesized from previously acylated phosphatidic acid, and is thus comprised of the same fatty acids as phosphatidic acid. However, there is a second biosynthetic pathway that contributes to cellular DAG concentrations. The hydrolysis of triacylglycerides (TAG) by one of a number of lipases creates a DAG, and this DAG does not necessarily share the same composition as phosphatidic acid.

The saturated fatty acid composition of lipid classes in mouse liver.

|  | % Total Saturated | 16:0 | 18:0 | Other |
|---|---|---|---|---|
| Phosphatidylcholine (PC) | 45.8 ± 1.7 | 33.4 ± 3.4 | 11.7 ± 2.9 | 0.7 ± 0.4 |
| Phosphatidylethanolamine (PE) | 40.6 ± 2.1 | 21.9 ± 1.6 | 18.1 ± 2.4 | 0.6 ± 0.3 |
| Phosphatidylserine (PS) | 47.3 ± 3.8 | 9.0 ± 1.9 | 37.0 ± 4.7 | 1.3 ± 0.7 |
| Diacylcglyceride (DG) | 32.1 ± 5.5 | 23.6 ± 4.1 | 5.3 ± 1.7 | 3.2 ± 1.0 |
| Triacylglyceride (TG) | 30.8 ± 4.7 | 27.0 ± 4.6 | 2.2 ± 0.9 | 1.6 ± 0.5 |

Anywhere there are two pathways contributing to the synthesis of a glycerolipid the composition of the glycerolipids should be able to determine the percentage contribution of each pathway and the total concentration of the lipid should scale the flux.

Although phosphatidylcholine synthesis is essential for both liver function and lipoprotein synthesis and export into plasma, the relative contribution of the two biosynthetic pathways for phosphatidylcholine synthesis to each of these processes is not fully understood. An initial step in the hepatic synthesis of lipoproteins involves constructing a phospholipid monolayer "skin," into which triacylglycerides are inserted. Based on this, it is believed that markers of alterations in phosphatidylcholine synthesis can be used to diagnose or predict dysregulations in liver-blood lipid exchange. Ideally, the markers of hepatic lipid accumulation would be present in the blood itself, enabling the facile measurement of liver lipid status in humans from a blood sample.

As stated above, liver phosphatidylcholine is synthesized by two pathways: (1) the CDP-choline pathway and (2) the PEMT pathway. These pathways use two previously acylated glycerolipids, 1,2-diacylglycerol in the case of the CDP-choline pathway, and phosphatidylethanolamine in the case of the PEMT pathway, as substrate for the biosynthesis of phosphatidylcholine. There is existing evidence that liver phosphatidylcholine synthesized by the PEMT pathway is comprised of molecular species that differ from the molecular species of phosphatidylcholine synthesized via the CDP-choline pathway (DeLong et al., *J Biol Chem* 274:29683-29688, 1999). It is now demonstrated herein that there are distinct and compositional differences between 1,2-DAG and phosphatidylethanolamine, the precursors to the CDP-choline and PEMT pathway, and that a modulation of either the CDP-choline pathway or the PEMT pathway produces a modulation of liver and plasma PC composition in a manner reflective of, and diagnostic for, the modulation.

There has never been a clear determination of (1) whether quantitative changes in liver phosphatidylcholine composition could diagnose or predict the balance of PEMT vs. CDP-choline activities in liver, (2) whether this diagnosis or prediction could be made from the assessment of the composition of plasma or serum lipids, and (3) whether these assessments could form the basis of diagnostics or prognostics for phenotypes related to phospholipid synthesis. The data included herein demonstrate that (1) that the origin of phosphatidylcholine biosynthesis (liver CDP-choline and PEMT) can be determined by measuring the composition of liver, plasma or serum phosphatidylcholine, (2) that the relative contribution of the CDP-choline and PEMT pathways to liver and plasma phosphatidylcholine can be determined by taking a simple ratio of the concentrations of stearic and palmitic acids in phosphatidylcholine, and that (3) this ratio is diagnostic and predictive for liver lipid accumulation and the ability of the liver to mobilize fatty acids, such as arachidonic acid and docosahexaenoic acid, into plasma.

Because 1,2 diacylglycerol and phosphatidylethanolamine have distinct fatty acid compositions, the composition of the resulting phosphatidylcholine can be used to assess its biosynthetic origin. Phosphatidylcholine derived from the CDP-choline pathway is rich in palmitic acid (16:0) while phosphatidylcholine derived from the PEMT pathway is rich in stearic acid (18:0). Thus, the ratio of 18:0 to 16:0 in PC is an excellent index of the relative contribution of the CDP-choline and PEMT pathways to total liver phosphatidylcholine content.

Other fatty acids found enriched in liver phosphatidylethanolamine include arachidonic acid (20:4n6), docosahexaenoic acid (22:6n3) and ether and plasmalogen-linked fatty acids, while fatty acids found enriched in the 1,2-DAG pool are oleic acid (18:1n9) and linoleic acid (18:2n6). Each of these fatty acids, when found in phosphatidylcholine in liver or plasma, can provide information about the proportion of PEMT pathway activity to CDP-choline pathway activity contributing to liver production of phosphatidylcholine.

The PEMT pathway is important for mobilizing lipid from the liver into plasma, and genetic alterations in this pathway can lead to severe liver damage (Waite et al., *J Nutr.* 132:68-71, 2002). This liver damage is only partially reversible with the addition of dietary choline, which increases the activity of the CDP-choline pathway. Conversely, a less common but significant perturbation of the CDP-choline pathway can also cause lipid accumulation in the liver. Thus, if there were an assay to discriminate how much of the plasma phosphatidylcholine was derived from the hepatic synthesis of phosphatidylcholine by the CDP-choline pathway versus the PEMT pathway, and whether a subject had a proper balance of the activity of these pathways, a researcher or clinician could assess the propensity for or presence of lipid accumulation in the liver.

Further, one could evaluate whether any specific intervention affects the biosynthesis of phosphatidylcholine by either pathway, and thus use this assay as a diagnostic. An advantage of this diagnostic would be that an assay of blood lipids would be informative about liver lipid metabolism, thus avoiding the need to take a liver biopsy. Additionally, this assay could determine whether the metabolism of an individual has been shifted, such that the diagnostic will have prognostic capabilities that biopsy-oriented diagnostics do not.

The compositional dissimilarity between phosphatidylcholine in the liver synthesized from the CDP-choline pathway and phosphatidylcholine synthesized from the PEMT pathway has been described previously (DeLong et al., *J Biol Chem* 274:29683-29688, 1999). It is believed that the majority of plasma phosphatidylcholine is derived from liver phosphatidylcholine pools. Certainly this is true for plasma lipids present in very low-density, intermediate-density and low-density lipoproteins, all of which are derived from liver lipid export.

The inventor has discovered that plasma phosphatidylcholine lipid composition predicts the lipid composition of phosphatidylcholine in liver with a high degree of confidence. Thus, this disclosure provides methods of assessing the lipid composition of liver PC by assessing the lipid composition of serum PC.

Measurement of these compounds, either from biological samples, or in silico (from a table or database) can be, among other things, used for:

(1) the assay of the activity of enzymes involved in the biosynthesis of phosphatidylcholine within the liver;

(2) the bulk process of phosphatidylcholine biosynthesis itself;

(3) the measurement of processes in which phosphatidylcholine biosynthesis is a component (either as a direct assay of the process or as a constituent part of a profile to assay this process);

(4) phenotypes or the propensity to express a phenotype that results from or is related to phosphatidylcholine biosynthesis, such as liver lipid accumulation, liver growth, or regeneration, hormone metabolism, and the mobilization of essential fatty acids from the liver in phosphatidylcholine, and (5) identification and testing/characterization of compounds or non-compound influences (such as exercise, dietary changes, nutritional treatment, and so forth) regarding their ability to influence (e.g., treat, detect, analyze, ameliorate, reverse, and/or prevent changes in) phosphatidylcholine biosynthesis or a phenotype influenced by phosphatidylcholine biosynthesis.

These measurements can be used to assess individuals or populations and to assess the results of an intervention, for instance an intervention by pharmacological, nutritional, toxicological, environmental, or genomic means. Further, these markers and profiles can be used to mine, parse, sort, filter, or otherwise investigate a database of lipid metabolites.

Although the invention has been described with reference to the presently preferred embodiment, it should be understood that various modifications can be made without departing from the spirit of the invention. Accordingly, the invention is limited only by the following claims.

What is claimed is:

1. A method of determining a contribution of a first pathway and a contribution of a second pathway, which is different from the first pathway, to biosynthesis of a lipid class in an individual, wherein the lipid class, which comprises a marker composition, is produced from a first precursor by the first pathway and from a second precursor by the second pathway, wherein the first precursor is different from the second precursor, comprising determining P1, wherein P1 is a level of a marker composition and, wherein the first precursor is transformed to said lipid class via the first pathway, determining P2, wherein P2 is a level of said marker composition, wherein said second precursor is transformed to the lipid class via the second pathway, wherein the first precursor is different from the second precursor and wherein the first pathway is different from the second pathway, determining TL, wherein TL is a level of the marker composition in the lipid class, and then calculating the contribution of the first pathway as (TL−P2)/(P1−P2) and the contribution of the second pathway as (TL−P1)/(P2−P1), thereby determining the contribution of the first pathway and the contribution of the second pathway to the biosynthesis of the lipid class.

2. The method of claim 1, wherein the marker composition is a SN-1 position fatty acid.

3. The method of claim 1, wherein the marker composition is a fatty acid selected from the group consisting of 16:0, 18:0, 18:1, 18:2, 20:4, and 22:6.

4. The method of claim 1, wherein the level of the marker composition is represented by the level of 18:0 or 16:0.

5. The method of claim 1, wherein the level of the marker composition is represented by the ratio of at least two fatty acids at SN-1 position.

6. The method of claim 1, wherein the level of the marker composition is represented by the ratio of 18:0 to 16:0.

7. The method of claim 1, wherein the level of the marker composition is represented by the ratio of any two of 18:0, 16:0, 18:1, 18:2, 20:4, and 22:6.

8. The method of claim 1, wherein the level of the marker composition is represented by the ratio of any three of 18:0, 16:0, 18:1, 18:2, 20:4, and 22:6.

9. The method of claim 1, wherein the lipid class is phosphatidylcholine.

10. The method of claim 1, wherein the lipid class is phosphatidylethanolamine, cholesterol ester, phosphatidylserine, phosphatidylinositol, cardiolipin, triacylglyceride, diacylglyceride, phosphatidic acid, free fatty acid, sphingomyelin, phosphatidylglycerol, or lysophospholipids.

11. The method of claim 1, wherein the lipid class is phosphatidylcholine, the first pathway is phosphatidylethanolamine-N-methyltransferase (PEMT) pathway, and the second pathway is CDP-choline pathway.

12. The method of claim 1, wherein the lipid class is phosphatidylcholine, the first pathway is phosphatidylethanolamine-N-methyltransferase (PEMT) pathway and the first precursor is phosphatidylethanolamine.

13. The method of claim 1, wherein the lipid class is phosphatidylcholine, the second pathway is CDP-choline pathway and the second precursor is selected from the group consisting of diacylglyceride, phosphatidic acid, and triacylglyceride.

14. The method of claim 1, wherein the lipid class is phosphatidylethanolamine, the first pathway is phosphatidylserine decarboxylase pathway and the second pathway is CDP-ethanolamine pathway.

15. The method of claim 1, wherein the lipid class is phosphatidylethanolamine, the first pathway is phosphatidylserine decarboxylase pathway and the first precursor is phosphatidylserine.

16. The method of claim 1, wherein the lipid class is in plasma.

17. The method of claim 1, wherein the lipid class is in liver.

18. The method of claim 1, wherein the lipid class is in brain, heart, mammary gland, or intestine.

19. The method of claim 1 wherein the marker composition is a fatty acid.

* * * * *